United States Patent [19]

Raifeld

[11] Patent Number: 5,216,145
[45] Date of Patent: Jun. 1, 1993

[54] ASYMMETRIC SYNTHESIS OF 3-SUBSTITUTED FURANOSIDE COMPOUNDS

[75] Inventor: Yuri E. Raifeld, Moscow, U.S.S.R.

[73] Assignee: American Cyanamid Company, Wayne, N.J.

[21] Appl. No.: 698,042

[22] Filed: May 10, 1991

[51] Int. Cl.$^5$ .................... C08B 37/00; C07H 1/00; C07H 3/00; C07H 15/00
[52] U.S. Cl. .................... 536/111; 536/18.2; 536/17.2; 536/17.5; 536/18.4; 536/18.7; 536/54; 536/55.3; 536/63; 536/18.1; 536/17.4; 536/124
[58] Field of Search .................... 536/18.6, 23, 24, 26, 536/22, 17.4, 18.4, 18.5, 18.1, 25, 27, 1.11, 18.2, 18.7, 17.2, 17.5, 54, 55.3, 63, 124

[56] References Cited

PUBLICATIONS

Fleet, G. W. et al., Tetrahedron, 1988, 44(2): 625–636.
Bravo, P. et al., J. Org. Chem., 1989, 54: 5171–5176.
Y. Gao et al., J. Amer. Chem. Soc., 1987, 109: 5765–5780.

*Primary Examiner*—Ronald W. Griffin
*Attorney, Agent, or Firm*—Kenneth J. Dow

[57] ABSTRACT

Novel processes, intermediates and reagents for the preparation of 3-substituted furanose or furanoside compounds of Formula I:

FORMULA I

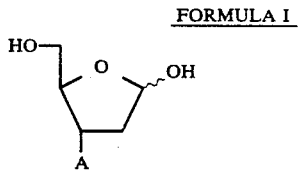

wherein M is hydrogen or alkyl ($C_1$–$C_3$), A is halogen or A may be selected from a moiety of the formula: OR, SR, $N_3$, SCR, OC-R or CN wherein R is hydrogen, branched or unbranched alkyl ($C_1$–$C_4$) or phenyl which compounds have antiviral and other biological activity.

7 Claims, No Drawings

ASYMMETRIC SYNTHESIS OF 3-SUBSTITUTED FURANOSIDE COMPOUNDS

FIELD OF THE INVENTION

The present invention is directed to novel processes, intermediates and reagents for the preparation of 3-substituted furanose or furanoside compounds useful as intermediates in the synthesis of various modified nucleosides having biological activity.

BACKGROUND OF THE INVENTION

The recent discovery of the reverse transcriptase inhibiting activity of various modified nucleosides and their actual and potential utility as therapeutic agents in the treatment of Acquired Immunodeficiency Syndrome (AIDS) related human immunodeficiency virus (HIV) infections, has stimulated interest in improved methods of preparing such modified nucleosides. Of particular interest are new methods of preparing 3-substituted 2',3'-dideoxyribonucleosides such as 3'-azido-3'-deoxythymidine (AZT) and 3'-deoxy-3'-fluorothymidine (FLT) which have been reported to be potent inhibitors of HIV-induced cytopathogenicity. Extensive studies on the synthesis and biological activity of 3'-azido, 3'-amino, and 3'-fluoro pyrimidine and purine 2',3'-dideoxyribonucleoside analogues have been reported.

In general, methods of producing such 3'-substituted nucleosides have proceeded along two separate paths: (1) substitution of the 3'-OH function in a 2'-deoxynucleoside, as in the case of the synthesis of AZT or FLT from thymidine, or (2) preparation of a 3-substituted furanoside compound followed by the coupling of a suitable purine or pyrimidine base such as thymine. The latter method has certain advantages since it uses simpler starting materials and it provides for the easy substitution of a number of nucleophiles at the 3'-position to provide intermediates suitable for efficient coupling with purine or pyrimidine bases. The latter method therefore provides the greatest possibilities for synthesis of 3'-substituted nucleosides in the large scale quantities.

Several methods for the synthesis of 3-substituted furanoside sugars have been described, but they are complicated, and they require multiple steps and expensive reagents. Fleet, G. W. et al; Tetrahedron 1988, 44(2) 625–636 describes the synthesis of methyl 5-O-tert-butyldiphenylsilyl-2-deoxy-α(β)-D-threo-pentofuranoside from D-xylose and its conversion to the azido, fluoro and cyano sugars followed by the subsequent coupling of these derivatives with protected thymine to give the thymidine compounds. Bravo, P. et al., J. Org. Chem. 1989, 54, 5171–5176 describes the asymmetric synthesis of the 3-fluorofuranoses starting from a compound of the formula:

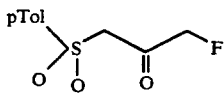

which is monoalkylated on the fluorinated carbon with allyl bromide. Removal of the auxiliary sulfinyl group followed by a reductive work-up and oxidative cleavage of the double bond afforded the 5-O-benzoyl-2,3-dideoxy-3-fluorofuranose.

The present invention describes and improved alternate method for the synthesis of the 3-substituted furanoses and furanosides. The process if uncomplicated, uses a small number of steps and simple, inexpensive starting materials.

SUMMARY OF THE INVENTION

This invention is an improved process for the asymmetric synthesis of 3-substituted furanoside compounds of the formula:

FORMULA I

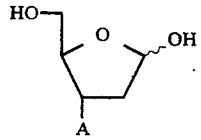

wherein M is hydrogen or alkyl ($C_1$-$C_3$), A is halogen or A may be selected from a moiety of the formula: OR, SR, $N_3$,

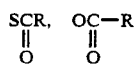

or CN wherein R is hydrogen, branched or unbranched alkyl($C_1$-$C_4$) or phenyl. The improved process may be depicted by the following reaction Scheme I:

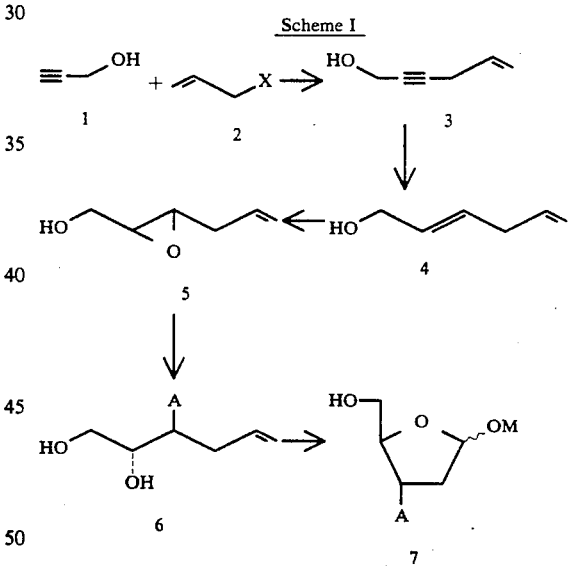

In the foregoing Scheme I, X may be chloride or bromide.

The present invention is also directed to a novel process of preparing fluorinating reagents of the formula:

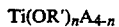

wherein n is an integer from one to three, R' is branched or unbranched alkyl ($C_1$-$C_4$) and A is as defined above.

DETAILED DESCRIPTION

In accordance with Scheme I, propargyl alcohol 1 is reacted with allyl chloride or allyl bromide 2 to afford alcohol 3. Reduction of 3 with lithium aluminum hydride yields olefin 4. Epoxidation of 4 gives oxirane 5. Regioselective oxirane ring opening of 5 by treatment with an appropriate nucleoplilic reagent having the substituent A gives diol 6 which is treated with ozone and then hydrogenated in the presence of 10% palladium on carbon to give the substituted pentose compound of formula 7.

In the preferred embodiment of the present invention, the 3-substituted furanoside sugars of Formula I are prepared by the following steps:

(a) Propargyl alcohol 1 is condensed with allyl chloride or allyl bromide 2 in water at pH 8–9 at a temperature of 65°–70° C. under stirring with CuCl or CuBr to yield hex-5-en-2-yn-1-ol 3;

(b) Compound 3 is then reduced by LiAlH$_4$ in tetrahydrofuran to yield the allyl alcohol, 4, trans-2,5-hexadien-1-ol;

(c) the allyl alcohol 4 is then asymmetrically epoxidized in the presence of diisopropyl-D-(-)-tartrate to yield the oxirane compound 5, 2R,3R-epoxyhex-5-en-1-ol;

(d) the oxirane compound 5 is then subjected to regioselective nucleophilic ring opening by treatment with an appropriate nucleoplilic reagent of the formula:

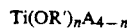

wherein n is an integer from 1 to 3, R' is branched or unbranched alkyl(C$_1$-C$_4$) and A is as defined above to yield the diol compound of formula 6;

(e) the diol compound 6 is then subjected sequentially to
 i) ozone;
 ii) reductive workup by hydrogenation with H$_2$ on palladium-on-carbon and;
 iii) alcoholysis to yield 3-substituted-2,3-dideoxy-D-erythropentosides of formula 7, as a mixture of α and β isomers.

As set forth above in step (c), the allyl alcohol compound 4 is asymmetrically epoxidized by the method of Y. Gao et al., *J. Amer. Chem. Soc.*, 109, 5765–5780 (1987), hereby incorporated by reference into the present application. This method produces epoxides from olefins in at least a 94% enantiomeric excess. Olefins can be converted to the corresponding epoxide on treatment with a catalytic amount of a catalyst prepared from a tartrate such as diethyl or diisopropyl tartrate and titanium (IV) isopropoxide. The best ratio of titanium/tartrate is 1:1.2. It is important to keep the reaction mixture free of moisture. Powdered activated molecular sieves work well. Solvents such as dichloromethane, toluene or isooctane can be used. Reactions are generally carried out at temperatures of about 31 20° C. All reactions are done in the presence of tert-butyl hydroperoxide (TBHP), although other peroxides may be used.

In general, the tartrate catalyst is prepared by mixing the chosen tartrate and titanium (IV) isopropoxide at −20° C. in a solvent such as methylene chloride whereupon either the olefinic alcohol or the tert-butyl hydroperoxide is added. In any case, the three ingredients are added and stirred for about 30 minutes before the last reagent is added whether it be the alcohol or the tert-butyl hydroperoxide. All reactions are carried out in the presence of powdered activated sieves. The 30 minutes of stirring is termed the "aging" period and is an important factor in obtaining high enantioselectivity.

In step (d) above, the oxirane compound 5 is subjected to regioselective nucleophilic ring opening by mild treatment with a reagent of the formula:

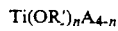

wherein n is an integer from 1 to 3, R' is branched or unbranched alkyl of 1 to 4 carbon atoms and A is defined above to yield the diol compound of formula 6.

The nucleophilic reagents of the formula Ti(OR')$_n$A$_{4-n}$ may conveniently be prepared from titanium (IV) alkoxides of the formula Ti(OR')$_4$ by reaction with an appropriate molar concentration of the corresponding acid, anhydride or trimethylsilyl ether compounds as follows:

where R" is hydrogen, CH$_3$CO, benzoyl or Si(CH$_3$)$_3$. For example titanium triisopropoxy chloride may be obtained by reacting titanium (IV) isopropoxide with trimethylsilylchloride. Titanium trisopopylazide may be obtained from titanium (IV) isopropoxide by reaction with HN$_3$ in pentane. Titanium triisopropyl thiobenzoate may be obtained by reacting titanium (IV) isopropoxide with thiobenzoic acid.

The preferred nucleophilic reagent, in the case where A is fluorine, is titanium (IV) difluorodiisopropoxide, [TiF$_2$(OiPr)$_2$], which can conveniently be prepared by adding titanium (IV) isopropoxide at 20°–25° C. to benzoyl fluoride or CH$_3$COF in hexanes. The product, titanium (IV) difluorodiisopropoxide, is collected by filtration in an inert atmosphere.

Where the substituent A is other than fluoride, the preferred nucleophilic reagent for the ring opening reaction is titanium (IV) triisopropoxide. This reagent was used for the regioselective ring opening of the epoxide compound of the formula:

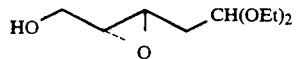

under the reactions conditions set forth in Table I:

TABLE 1

| Regioselective ring opening of 1,1-diethoxy-3R,4R-epoxypentane-5-ol by (i-PrO)$_3$TiA | | | | |
|---|---|---|---|---|
| | Reaction Conditions | | | Composition of the resulting mixture, % |
| A | t/h | solvent | Yield, %$^b$ | (2) | (3) |
| OAc | 1 | CHCl$_3$ | 95 | >98 | <2 |
| OTol | 1 | CHCl$_3$ | 90 | >98 | <2 |
| Cl | 1 | C$_6$H$_6$ | 85 | >85 | 15 |
| SCOPh | 1 | CHCl$_3$ | 80 | >98 | <2 |
| N$_3$ | 1.5 | CHCl$_3$ | 95 | >92 | 8 |

$^b$A summary yield of the 3- and 4-substituted acetals after the workup

The foregoing reaction conditions are equally applicable for the regioselective ring opening of compound 5, 2R,3R-epoxyhex-5-en-1-ol. Thus, the titanium (IV) triisopropoxide compounds make it possible to provide for mild regioselective oxirane ring opening by the nucleophilic group A with high efficiency. This method may be used for a wide variety of oxirane ring opening reactions where A is any nucleophilic group.

The nucleophilic ring opening reaction (step d) may be carried out in a variety of solvents including benzene, toluene, chloroform, methanol or a mixture thereof. Generally, a 1.5 mol excess of the reagent is preferable. Temperature conditions may range from 0°–130° C. with the preferred temperature being 80°–120° C. where the reaction generally proceeds in less than one hour to greater than 90 percent conversion. Final products may be isolated from the reaction mixture by chromatography.

In Step (e) above, the diol compound of formula 6 is dissolved in methyl alcohol and while cooling at $-\alpha°$ to $-70°$ C. dry ozone is added through a bubbler until the reaction is complete. After warming to 0° C., palladium-on-carbon is added and the reaction subjected to an atmosphere of hydrogen until uptake is complete. The addition of hydrochloric acid completes the glycosidation to yield the 3-substituted-2,3-dideoxy-erythropentose compound of formula 7, as a mixture of $\alpha$ and $\beta$ isomers.

Upon further study of the specification and appended claims, further objects and advantages of this invention will become apparent to those skilled in the art.

This invention will be described in greater detail in conjunction with the following, non-limiting specific examples.

EXAMPLE 1

Hex-5-en-2-yn-1-ol

To a stirred mixture of 250 ml of saturated sodium chloride solution, 1 ml of hydrochloric acid, 8 g of copper (I) chloride and 28 g of propargyl alcohol is added at room temperature a 40% sodium hydroxide solution until the pH is adjusted to 9. The reaction mixture is heated in a bath of 70° C. and a solution of 120 ml of allyl chloride in 80 ml of methyl alcohol added dropwise. The pH of the reaction mixture is carefully maintained between 8 and 9 by the coaddition of 40% sodium hydroxide, as needed. Following complete addition of the allyl chloride solution and with the pH between 8–9 the reaction mixture is stirred at 70° C. for 3.5 hours. The flask is cooled to room temperature and hydrochloric acid added until the pH is 2. The organic phase is separated and the aqueous layer extracted with 3×50 ml of ether. The organic layers are combined and the volatiles removed in vacuo to afford an oil which is vacuum distilled to yield 45 g of the desired product as a water white liquid, BP 67°–68° C./10 mm $n_D^{20}$ 1.4670.

$^{13}$C-NMR: 137.69(C-5), 115.98(C-6), 82.65 and 81.54(C-2 and C-3), 50.59(C-1), 23.21(C-4).

Anal. Calc'd for $C_6H_8O$: C, 74.97; H, 8.39 Found: C, 75.11; H, 8.18.

EXAMPLE 2

Trans-2,5-hexadien-1-ol

To a stirred mixture of 3.8 g of lithium aluminum hydride in 150 ml of tetrahydrofuran, cooled to 0° C. is added dropwise a solution of 9.6 g of the product of Example 1 in 50 ml of tetrahydrofuran. Following complete addition the cooling is removed and the temperature allowed to reach room temperature followed by an additional 30 minutes of stirring. The temperature is raised to 45° C. for an additional 3 hours followed by cooling to 0° C. A 100 ml volume of saturated ammonium chloride is carefully added dropwise and the resulting mixture filtered. The filter cake is washed with 3×20 ml of diethyl ether and the combined filtrate dried over MgSO$_4$. The volatiles are removed in vacuo to a residue which is vacuum distilled to afford 7.9 g of the desired product as a water white liquid, BP 70°–72° C./15 mm, $n_D^{20}$ 1.4530. $^{13}$C-NMR: 137.57(C-5), 132.01 and 128.89(C-2, C-3), 115.40(C-6), 63.00(C-1), 36.80(C-4).

Anal. Calc'd for $C_6H_{10}O$: C, 73.43; H, 10.27. Found: C, 72.98; H, 10.01.

EXAMPLE 3

2R,3R-Epoxyhex-5-en-1-ol

A mixture of 3.0 g of 4A powdered, activated molecular sieves and 300 ml of dry methylene chloride is cooled to $-20°$ C. and 2.81 g (2.36 ml) of diisopropyl D-(-)-tartrate and 2.84 g (2.36 ml) of titanium (IV) isopropoxide added sequentially with continued stirring. The reaction mixture is stirred at $-20°$ C. as 40 ml of 5 M TBHP in methylene chloride is added over 5 minutes. Stirring is continued at $-20°$ C. for 30 minutes followed by the dropwise addition of a solution of 9.8 g of the product of Example 2 in 50 ml of methylene chloride while keeping the reaction temperature between $-25°$ and $-20°$ C. The mixture is stirred for 8–10 hours at $-25°$ to $-20°$ C., followed by quenching with 8 ml of a 10% aqueous solution of sodium hydroxide saturated with sodium chloride (10 g NaCl+10 g NaOH+95 ml of water), previously cooled to $-20°$ C. Ether is added to afford a 10% V/V reaction mixture. The cooling bath is removed and the stirring reaction mixture allowed to warm to 10° C. followed by an additional 10 minutes of stirring. While stirring, 8 g of magnesium sulfate and 1 g of diatomaceous earth is added. Stirring is continued for an additional 15 minutes followed by filtering through a pad of diatomaceous earth. The cake is washed with ether (3×50 ml). The combined filtrates are dried over magnesium sulfate and the volatiles evaporated in vacuo to afford a residue which is vacuum distilled to give 8.9 g of the desired product, BP 85°–87° C./10 mm $n_{20}^D$ 1.4458 $[\alpha]_D^{20}$+23.2 (c 10, CH$_3$OH). $^{13}$C-NMR: 134.49(C-5), 117.28(C-6), 62.69(C-1), 58.65(C-2), 55.12(C-3), 36.45(C-4).

Anal. Calc'd for $C_6H_{10}O_2$: C, 63.13; H, 8.83 Found: C, 62.88; H, 8.19

EXAMPLE 4

Titanium (IV) difluorodiisopropoxide

To a stirred mixture of 37.4 g of benzoyl fluoride in 100 ml of hexane, while cooling in a 20°–25° C. bath is added dropwise 28.4 g of titanium (IV) isopropoxide. The reaction proceeds with an increase in temperature. A white solid forms, which is filtered in an inert atmosphere, then dried under vacuum to afford 13.6 g of the desired product as a white fine powder.

EXAMPLE 5

2R,3S-3-Fluorohex-5-en-1,2-diol

A mixture of 13.6 g of titanium (IV) difluorodiisopropoxide in 180 ml of dry toluene is heated to reflux with stirring in a 120° C. oil bath. A solution of 5.8 g of 2R,3R-epoxyhex-5-en-1-ol in 10 ml of dry toluene is added dropside to the refluxing reaction mixture. The bath is removed following complete addition and stirring continued while the temperature lowers to 25°–30° C. A 15 ml volume of saturated sodium bicarbonate is added with vigorous stirring. Stirring is continued over 2 hours and the pH is neutral to slightly alkaline. Additional saturated sodium bicarbonate added as needed to adjust the pH. The reaction mixture is filtered through diatomaceous earth, and the cake washed with acetone. The combined filtrates are dried with MgSO$_4$ and the volatiles removed in vacuo. The residue is purified by chromatography on silica gel by elution with 50:1 chloroform-isopropyl alcohol to afford 3.4 g of the desired product as a white crystalline solid, m.p. 37°–38° C. TLC (9:1 chloroform-isopropyl alcohol) $R_F=0.41$.

$^{13}$C-NMR: 134.85(d, $J_{C-F}$ 3.5Hz, C-5), 117.62(C-6), 93.52(d, $J_{C-F}$ 171.6Hz, C-3), 73.30(d, $J_{C-F}$ 23.1Hz, C-2), 63.33(d, $J_{C-F}$ 5.5Hz, C-1), 35.98(d, $J_{C-F}$ 21.1Hz, C-4).

Anal. Calc'd for $C_6H_{11}O_2F$: C, 53.72; H, 8.27; F, 14.17 Found: C, 53.92; H, 8.01; F, 13.28.

EXAMPLE 6

Methyl-3-fluoro-2,3-dideoxy-α,β-D-erythropentofuranoside

A solution of 1.5 g of 2R,3S-3-fluorohex-5-en-1,2-diol is dissolved in 150 ml of methyl alcohol and cooled to $-60°--70°$ C. Oven dried ozone is bubbled through the reaction mixture for 3 hours. The reaction mixture is allowed to warm to 0° C. and 0.05 g of palladium-on-carbon added. While stirring 250 ml of hydrogen is absorbed. The reaction mixture is filtered and 1 ml of 10% HCl in methyl alcohol added. When the reaction is complete as shown by TLC (10:1 chloroform-methanol), the reaction mixture is neutralized with dry potassium carbonate, filtered and evaporated to give 1.0 g of the desired product as a mixture.

$^{13}$C-NMR: 106.27(C-1,β); 105.84(C-1,α), 95.55(d, $J_{C-F}$ 175.6Hz, C-3-β), 94.58(d, $J_{C-F}$ 177.6Hz, C-3-α), 86.31(d, $J_{C-F}$ 22.6Hz, C-4-β), 85.51(d, $J_{C-F}$ 23.6Hz, C-4-α), 63.15(d, $J_{C-F}$ 10.0Hz, C-5-β), 62.44(d, $J_{C-F}$ 9.6Hz, C-5-α), 55.40(-OMe-β), 54.68(-OMe-α), 40.40(d, $J_{C-F}$ 21.6Hz, C-2-β), 40.13(d, $J_{C-F}$ 21.1Hz, C-2-α).

Anal. Calc'd for $C_6H_{11}O_3F$: C, 47.99; H, 7.38; F, 12.65 Found: C, 47.15; H, 6.69; F, 11.80

We claim:

1. A process for preparing a compound of the formula:

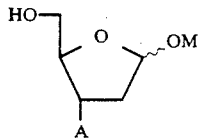

wherein M is selected from the group consisting of hydrogen and alkyl ($C_1$-$C_3$), A is a nucleophilic substituent selected from the group consisting of halogen and moieties of the formula:

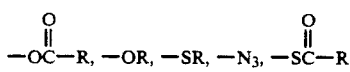

and CN wherein R is selected from the group consisting of hydrogen, branched and unbranched alkyl ($C_1$-$C_4$) and phenyl; which comprises:

(a) reacting a compound of the formula:

wherein X is selected from chloride and bromide, with propargyl alcohol to form hex-5-en-2-yn-1-ol;

(b) reacting the product of step (a) with lithium aluminum hydride to form 2,5-hexadien-1-ol;

(c) reacting the product of step (b) in the presence of diisopropyl-D-tartrate to form 2R,3R-epoxyhex-5-en-1-ol;

(d) reacting the product of step (c) with a suitable reagent having the nucleophilic substituent A as defined hereinabove, to form a compound of the formula:

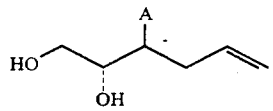

(e) reacting the product of step (d) with ozone followed by catalytic reduction with hydrogen over palladium-on-carbon and recovering a compound of the formula:

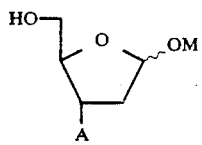

2. A process according to claim 1, wherein the suitable reagent of step (d) has the formula:

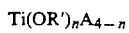

wherein n is defined as an integer from 1 to 3; R' is selected from branched and unbranched alkyl ($C_1$-$C_4$) and A is selected from the group consisting of F, Cl, Br, I, moieties of the formula:

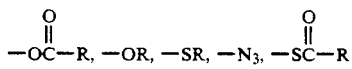

and CN wherein R is selected from hydrogen, branched and unbranched alkyl ($C_1$-$C_4$) and phenyl.

3. A process according to claim 2 wherein R' is defined as isopropyl, n is 2 and A is fluorine.

4. A process according to claim 2 wherein R' is defined as isopropyl, n is 1 and A is fluorine.

5. A process according to claim 2 wherein R' is defined as isopropyl, n is 1 and A is $-N_3$.

6. A process for preparing a compound of the formula:

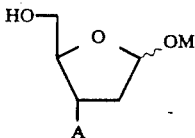

wherein M is selected from hydrogen and alkyl ($C_1$—$C_3$), A is a nucleophilic substituent selected from the group consisting of halogen, moieties of the formula:

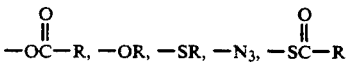

and CN wherein R is selected from hydrogen, branched and unbranched alkyl ($C_1$-$C_4$) and phenyl; which comprises:

(a) reacting a compound of the formula:

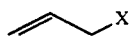

wherein X is selected from chloride and bromide with propargyl alcohol to form hex-5-en-2-yn-1-ol;

(b) reacting the product of step (a) with lithium aluminum hydride to form 2,5-hexadien-1-ol;

(c) reacting the product of step (b) in the presence of diisopropyl-D-tartrate at −30° C. to −20° C. for 8-10 hours to form 2R,3R-epoxyhex-5-en-1-ol;

(d) reacting the product of step (c) with a reagent of the formula:

Ti(OR')$_n$A$_{4-n}$ wherein n is an integer from 1 to 3; R' is selected from branched and unbranched alkyl(C$_1$-C$_4$) and A is as defined above to form a compound of the formula:

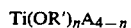

(e) reacting the product of step (d) with ozone followed by catalytic reduction with hydrogen over palladium-on-carbon and recovering a compound of the formula:

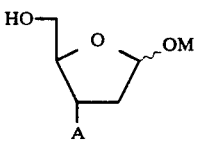

7. A process according to claim 6 wherein R' is defined as isopropyl, n is 2 and A is fluorine.

* * * * *